United States Patent [19]

Horiguchi et al.

[11] 4,328,314

[45] May 4, 1982

[54] PROCESS FOR PRODUCING PLASMINOGEN ACTIVATOR

[75] Inventors: Sadayuki Horiguchi; Akio Hasegawa; Hajimu Sakamoto, all of Fuji, Japan

[73] Assignee: Asahi Kasei Kogyo Kabushiki Kaisha, Osaka, Japan

[21] Appl. No.: 97,284

[22] Filed: Nov. 26, 1979

[30] Foreign Application Priority Data

Nov. 24, 1978 [JP] Japan ................................ 53-144234

[51] Int. Cl.³ ............................................... C12N 9/48
[52] U.S. Cl. ..................................... 435/212; 435/240
[58] Field of Search ........................ 435/212, 215, 240

[56] References Cited

U.S. PATENT DOCUMENTS 4,232,124 11/1980 Mann ................................... 435/215

Primary Examiner—Lionel M. Shapiro
Attorney, Agent, or Firm—Sughrue, Mion, Zinn, Macpeak and Seas

[57] ABSTRACT

In the production of plasminogen activator from animal cells in a nutrient solution, the addition of a large amount of fumaric acid, malic acid, succinic acid, and/or glycolic acid to the nutrient solution brings about a 30 to 180% increase in the amount of plasminogen activator produced.

9 Claims, 3 Drawing Figures

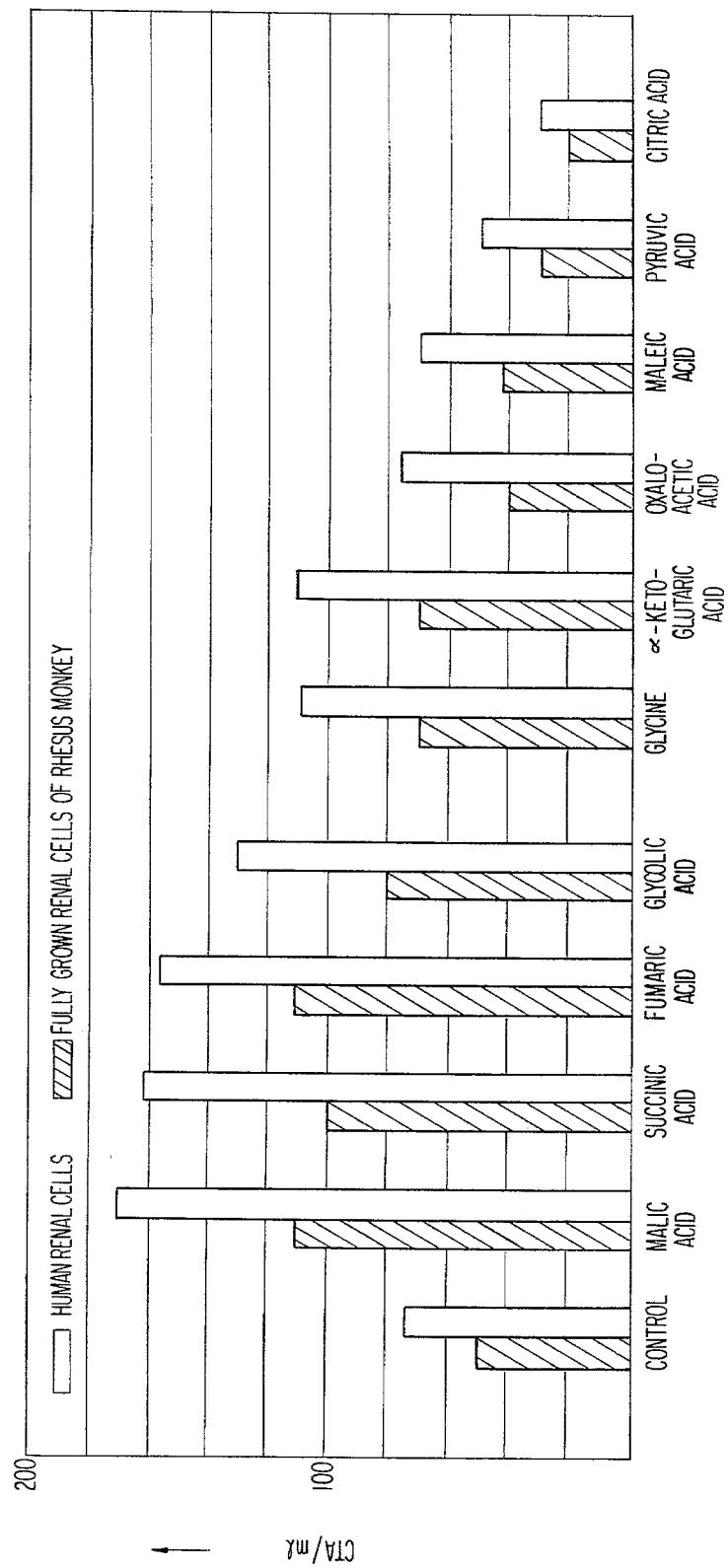

4,328,314

PROCESS FOR PRODUCING PLASMINOGEN ACTIVATOR

BACKGROUND OF THE INVENTION

1. Field of the Invention

This invention relates to a process for producing plasminogen activator in high yields utilizing animal cells.

2. Description of the Prior Art

Isolation and purification from human urine has previously been well known as a commercial process for producing plasminogen activator as described in W. F. White, *Biochemistry*, 5 2160, 1966. This conventional process, however, has the defect that the quality of human urine as a raw material is not uniform, the handling of urine poses a hygienic problem, and it is difficult to collect large quantities of urine from healthy persons.

Animal cells are known to provide plasminogen activator, as reported by Bernik et al in *J. Lab. & Clin. Med.*, 70 650 (1967). The Bernik procedure is not satisfactory for producing plasminogen activator on an industrial scale due to its low yields. However, it was believed that if yields could be improved the process of using animal cells to produce plasminogen activator could be adapted to an industrial scale and it would be possible to supply large quantities of raw material of uniform quality without the risk of contamination. Thus we desired to establish a technique which would render the use of animal cells commercially acceptable.

Extensive investigations have been directed to a process for producing plasminogen activator using animal cells. These investigations have led to the discovery that when an organic acid selected from fumaric acid, malic acid, succinic acid and glycolic acid is present in the aqueous nutrient solution with which animal cells are contacted to produce plasminogen activator, the amount of activator increases strikingly.

SUMMARY OF THE INVENTION

The present invention provides a process for producing plasminogen activator which comprises contacting animal cells having the ability to produce plasminogen activator with an aqueous nutrient solution, said aqueous nutrient solution containing an organic acid selected from the group consisting of fumaric acid, malic acid, succinic acid and glycolic acid.

BRIEF DESCRIPTION OF THE ACCOMPANYING DRAWINGS

FIG. 1 is a bar graph showing the results obtained in Example 1 of the present application in which the organic acids are shown on the horizontal and the amount of plasminogen activator produced is on the vertical;

FIG. 2 is a graph showing the results obtained in Example 3 of the present application in which the abscissa shows the concentrations of the organic acids used and the ordinate shows the amounts of plasminogen activator produced; and FIG. 3 is a graph showing the results obtained in Example 4 of the present application in which the abscissa shows the concentrations of the organic acids used and the ordinate shows the amounts of plasminogen activator produced.

DETAILED DESCRIPTION OF THE INVENTION

Figure 3:
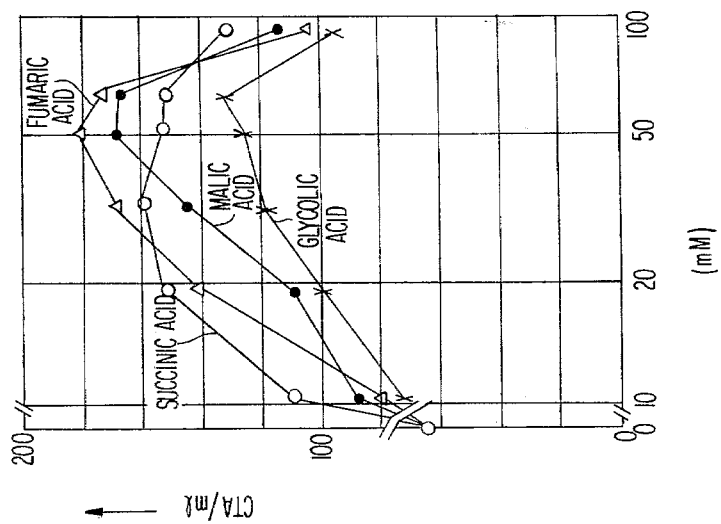

The cells used in this invention are animal cells having the ability to produce plasminogen activator. Examples of such cells include cells derived from the kidneys of an African green monkey, cells derived from the kidneys of a Rhesus monkey, cells derived from human embryonic kidneys, cells derived from the lungs of a human fetus, cells derived from a human embryo, cells derived from the skin of a human fetus, cells derived from a human placenta, cells derived from a human adult spleen, cells derived from human adult kidneys, cells derived from human adult lungs, cells derived from the human adult thyroid gland, cells derived from the heart of a human fetus, cells derived from the ureter of a human fetus, cells derived from the heart of a human adult, and cells derived from the ureter of a human adult. Of these cells, renal cells are particularly preferred. Preferably, these cells are supplied for use in the present invention after they are cultivated by methods usually employed for the cultivation of animal cells, for example, by the method described in *TISSUE CULTURE*, edited by Jyunnosuke Nakai et al., and published by Asakura Shoten in 1976 (a Japanese-language publication); and *Tissue Cultures in Biological Research* by G. Penso and D. Balducci, Elsevier Publishing Co., 1963.

As noted plasminogen activator has been produced by contacting animal cells with an aqueous nutrient solution containing carbon sources, nitrogen sources and optionally inorganic salts and/or other additives. A representative nutrient solution is that used by Bernik et al and the composition thereof is described in Table 1 herebelow. In the Examples, such a nutrient solution was employed as a basic composition. The composition of the nutrient solution employed in the present invention is not limited as long as it contains the basic nutrients (i.e., carbon and nitrogen sources) required to sustain the cells and the acids which are the characteristic feature of the present invention. Suitable carbon sources include glucose, maltose and sucrose. Suitable nitrogen sources are organic nitrogen sources, and amino acid mixtures and/or hydrolysis products of proteins are particularly preferred for the purpose. Such proteins may be animal or vegetable and include, for example, casein, soybean protein, lactalbumin and an animal protein. Suitable inorganic acid salts include salts consisting of a cation of calcium, potassium, sodium, iron, etc., and an anion of chlorine, sulfuric acid, carboxylic acid, phosphoric acid, nitric acid, etc. In addition to the compounds described above, vitamin coenzymes and other organic additives may be used.

The novel feature of the present invention is that an organic acid selected from the group consisting of fumaric acid, malic acid, succinic acid and glycolic acid is added to the aqueous nutrient solution, and the addition of these particular organic acids leads to a striking increase in the amount of plasminogen activator produced. Naturally, the acids can be used in combination. Mere addition of these organic acids to the nutrient suffices. Generally, the organic acids prove to be effective when added in an amount of 1 to 120 millimols, preferably 10 to 93 millimols, per liter of the aqueous nutrient solution. It has been discovered that when each of fumaric acid, succinic acid, malic acid and glycolic acid is used in these amounts, the amount of plasminogen activator produced is more than 131%, 177%, 142% or 115%, respectively, of that obtained without addition of the acids. In particular, fumaric acid and malic acid provide a marked increase in the amount of plasminogen activator of more than 269%.

Usually, the production of the aforesaid activator is performed using at least 0.2 ml, preferably 0.3 to 0.4 ml, of the aqueous nutrient solution per 100,000 cells at a temperature of from 15° to 45° C., preferably from 25° to 40° C. During the production, the pH of the nutrient solution is adjusted to 5 to 9, preferably 6 to 8. The period required for the productfion is usually 4 to 30 days, but may exceed 30 days. Since the speed of production gradually decreases in the later stage of production, the period which provides the best efficiency is chosen for commercial production.

The plasminogen activator is released from the cells into the aqueous nutrient solution under the aforesaid conditions. The amount of the activator produced is measured by a plate method in accordance with the procedure of Nishizaki and Kawamura, *Study of Pharmaceuticals* (a Japanese-language publication, Vol. 5, page 295, 1974) and J. Plong et al, *Biochem. Biophys. Acta*, 24 278, 1957. When the desired amount of activator or time is reached, the aqueous nutrient solution is collected, and the activator is recovered. The plate method is briefly summarized below:

Control solutions containing various concentrations of plasminogen activator and a test solution are dropped in a given amount onto a fibrin plate formed by coagulating a fibrinogen solution containing plasminogen with the addition of thrombin. After incubation of the plate at 37° C. for 20 hours, the diameter of the dissolved spots thus formed is measured. A calibration curve of the square of the diameter and the concentration of plasminogen activator is made based on the control solutions. The concentration of plasminogen in the test solution can be determined by repeating the procedure with the sample and comparing the result with the calibration curve.

Recovery of the plasminogen activator can be performed by, for example, adsorption, salting out, dialysis, chromatography, and gel filtration, either singly or in combination, which methods are usually employed for the recovery of the activator. Specifically, there can, for example, be used an adsorption method using hydroxyapatite, barium sulfate, etc., a salting-out method using ammonium sulfate, sodium chloride, sodium sulfate, ammonium chloride, etc., a chromatographic method using diethylaminoethyl cellulose, etc., a gel filtration method using acrylamide gel, modified dextran gel, etc., and the methods disclosed in Japanese Patent Publication No. 10232/73 and U.S. Pat. No. 4,028,187. The substance thus obtained dissolves a fibrin gel in the presence of plasminogen but does not dissolve a fibrin gel in the absence of plasminogen. Thus, the substance is capable of activating plasminogen to dissolve fibrin gel and is a plasminogen activator (cf. *Proteinases in Mammalian Cells and Tissues*, edited by A. J. Barrett, North-Holland Publishing Co., (1977)).

The process of this invention eliminates the defects of the conventional process in which the concentration of the starting urine is low, urine of stable quality is difficult to collect from healthy humans, and the hygienic problems. According to the invention, a starting material having a stable uniform quality can be supplied stably in high concentrations and in large quantities, and a superior commercial process for producing plasminogen activator is provided.

The following Examples illustrate the present invention more specifically.

EXAMPLE 1

To a solution having the formulation shown in Table 1 each of fumaric acid, malic acid, succinic acid, glycolic acid, glycine, α-ketoglutaric acid, oxaloacetic acid, maleic acid, pyruvic acid and citric acid was added 60 millimols per liter of the solution. Fully grown renal cells of Rhesus monkeys (Flow Laboratories, Inc.) and human renal cells (Flow Laboratories, Inc.) were each maintained at 37° C. for 20 days in each of the nutrient solutions in an atmosphere of air containing 5% of carbon dioxide gas. The amount of plasminogen activator in the solution was measured and the results are shown in FIG. 1. It is seen from FIG. 1 that when malic acid, succinic acid, fumaric acid and glycolic acid are present, the amount of plasminogen activator produced is 160 to 227% of that obtained as control, i.e., when no organic acids were used. The amounts of plasminogen activator are expressed in CTA units as stipulated by the Committee on Thrombolytic Agents of the National Heart Institute, as described in A. J. Johnson, *Thromb. Diath. Haemor.*, 21, p. 259 (1969).

TABLE 1

|  | mg/l |
|---|---|
| NaCl | 8000.0 |
| KCl | 400.0 |
| $Na_2HPO_4 \cdot 2H_2O$ | 60.0 |
| $KH_2PO_4$ | 60.0 |
| $MgSO_4 \cdot 7H_2O$ | 100.0 |
| $CaCl_2$ (anhydrous) | 140.0 |
| Glucose | 1000.0 |
| $MgCl_2 \cdot 6H_2O$ | 100.0 |
| $NaHCO_3$ | 350.0 |
| Lactoalbumin hydrolyzate | 5000.0 |

EXAMPLE 2

Fully grown renal cells of African green monkeys (Flow Laboratories, Inc.) were maintained at 37° C. for 15 days in a solution having the formulation shown in Table 2 in an atmosphere of air containing 5% of carbon dioxide gas. The plasminogen activator in the solution was measured and the results are shown in Table 3 together with the results of a control test in which fumaric acid was not used. It is seen from the table that when fumaric acid was added to the nutrient solution, the amount of the plasminogen activator was 1.8 to 2.1 times as large as that obtained in the control. The amount of the activator is expressed in CTA units as in Example 1.

TABLE 2

|  | mg/l |
|---|---|
| NaCl | 8000.0 |
| KCl | 400.0 |
| $Na_2HPO_4 \cdot 2H_2O$ | 60.0 |
| $KH_2PO_4$ | 60.0 |
| $MgSO_4 \cdot 7H_2O$ | 100.0 |
| $CaCl_2$ (anhydrous) | 140.0 |
| Glucose | 1000.0 |
| $MgCl_2 \cdot 6H_2O$ | 100.0 |
| $NaHCO_3$ | 350.0 |
| Lactoalbumin hydrolyzate | 5000.0 |
| Fumaric acid | 30 mM |

TABLE 3

| | Amount of Activator (CTA/ml) | | |
|---|---|---|---|
| | Number of Days Elapsed | | |
| | 5 | 10 | 15 |
| Fumaric Acid | | | |
| Present | 60 | 110 | 130 |
| Absent | 34 | 60 | 62 |

TABLE 4

| Organic Acid | Amount of Acid (mM) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Fumaric Acid | 0 | 30 | 30 | 30 | 0 | 0 | 0 | 20 | 0 | 20 | 20 | 15 |
| Succinic Acid | 0 | 30 | 0 | 0 | 30 | 30 | 0 | 20 | 20 | 0 | 20 | 15 |
| Malic Acid | 0 | 0 | 30 | 0 | 30 | 0 | 30 | 20 | 20 | 20 | 0 | 15 |
| Glycolic Acid | 0 | 0 | 0 | 30 | 0 | 30 | 30 | 0 | 20 | 20 | 20 | 15 |
| Amount of Activator (CTA/ml) | 52 | 141 | 149 | 140 | 138 | 135 | 125 | 135 | 135 | 130 | 125 | 120 |

EXAMPLE 3

Figure 2:
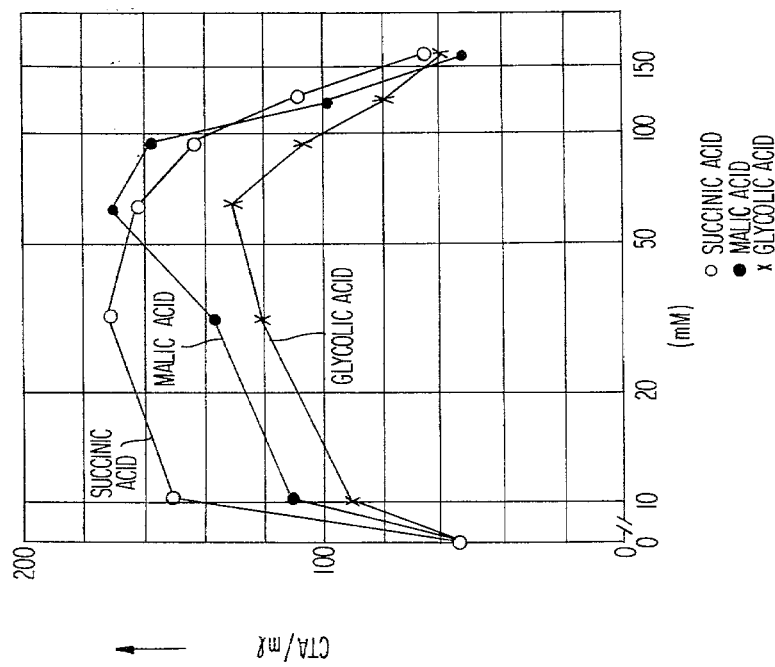

Succinic acid, malic acid, and glycolic acid were each added in various concentrations to a solution having the formulation shown in Table 1. Fully grown renal cells of African green monkeys (Flow Laboratories, Inc.) were maintained at 37° C. for 20 days in each of the resulting nutrient solutions in an atmosphere of air containing 5% of carbon dioxide gas. The plasminogen activator in the solutions was determined and the results are shown in FIG. 2. It is seen that a marked increase in the amount of plasminogen activator was achieved when the organic acids were used in a concentration ranging from 10 to 120 mM.

EXAMPLE 4

Fumaric acid, malic acid, succinic acid, and glycolic acid were each added in various concentrations to a solution having the formulation shown in Table 1. Fully grown renal cells of humans (Flow Laboratories, Inc.) were maintained at 37° C. for 18 days in each of the resulting nutrient solutions in an atmosphere of air containing 5% of carbon dioxide gas. The plasminogen activator in the solutions was determined, and the results are shown in FIG. 3. It is seen that an especially marked increase in the amount of plasminogen activator is achieved when the organic acids are used in a concentration in the range of 10 to 93 mM.

EXAMPLE 5

The same procedures as in Example 4 were repeated except that the acids were used in various combinations as shown in Table 4. The results obtained are also shown in Table 4.

Thus a marked increase in the amount of plasminogen activator is achieved using the acids in combination as well as using them alone. Further, when fumaric acid is used in combination with malic acid, a particularly high amount of plasminogen activator was achieved.

While the invention has been described in detail and with reference to specific embodiments thereof, it will be apparent to one skilled in the art that various changes and modifications can be made therein without departing from the spirit and scope thereof.

What is claimed is:

1. In a process for producing plasminogen activator which comprises contacting animal cells having the ability to produce plasminogen actovator with an aqueous nutrient solution, the improvement wherein said aqueous nutrient solution contains 1 to 120 millimoles per liter of aqueous nutrient of an organic acid selected from the group consisting of fumaric acid, malic acid, succinic acid and glycolic acid.

2. The process of claim 1, wherein the concentration of said organic acid is 10 to 93 millimols per liter of said aqueous nutrient solution.

3. The process of claim 1, wherein said cells are renal cells.

4. The process of claim 1, wherein said acid is fumaric acid.

5. The process of claim 1, wherein said acid is malic acid.

6. The process of claim 1, wherein said acid is succinic acid.

7. The process of claim 1, wherein said acid is glycolic acid.

8. The process of claim 1, wherein a combination of said acids is used.

9. The process of claim 1, wherein a combination of fumaric acid and malic acid is used.

* * * * *